(12) United States Patent
Shen et al.

(10) Patent No.: US 9,556,422 B2
(45) Date of Patent: Jan. 31, 2017

(54) HIGHLY GLYPHOSATE-RESISTANT MUTATED GENE, METHOD OF MODIFICATION AND USE THEREOF

(75) Inventors: Zhicheng Shen, Hangzhou (CN); Chaoyang Lin, Hangzhou (CN); Xiaoli Xu, Hangzhou (CN); Xinlan Li, Hangzhou (CN)

(73) Assignee: HANGZHOU RUIFENG BIOTECHNOLOGY LIMITED INC., Hangzhou, Zhejiang Province (CN)

( * ) Notice: Subject to any disclaimer, the term of this patent is extended or adjusted under 35 U.S.C. 154(b) by 67 days.

(21) Appl. No.: 13/979,901

(22) PCT Filed: Jan. 17, 2012

(86) PCT No.: PCT/CN2012/070440
§ 371 (c)(1),
(2), (4) Date: Sep. 12, 2013

(87) PCT Pub. No.: WO2012/097720
PCT Pub. Date: Jul. 26, 2012

(65) Prior Publication Data
US 2014/0298533 A1 Oct. 2, 2014

(30) Foreign Application Priority Data
Jan. 17, 2011 (CN) .......................... 2011 1 0009329

(51) Int. Cl.
*C12N 9/10* (2006.01)
*C12N 15/82* (2006.01)
*C07K 14/415* (2006.01)

(52) U.S. Cl.
CPC ........... *C12N 9/1092* (2013.01); *C07K 14/415* (2013.01); *C12N 15/8275* (2013.01); *C12Y 205/01019* (2013.01)

(58) Field of Classification Search
CPC .............. A01H 1/00; A01H 5/00; C12N 1/21; C12N 15/63; C12N 5/04; C12N 9/10; C12P 21/00
See application file for complete search history.

(56) References Cited

U.S. PATENT DOCUMENTS

| 7,960,616 B2 * | 6/2011 | Heinrichs | .......... C12N 15/8275 435/252.3 |
| 2003/0049814 A1 | 3/2003 | Andrews et al. | |
| 2003/0084473 A1 | 5/2003 | Gocal et al. | |
| 2007/0169218 A1 * | 7/2007 | Carr | .................. C12N 15/8275 800/278 |

FOREIGN PATENT DOCUMENTS

| CN | 1359422 A | | 7/2002 | |
| CN | 101619318 A | * | 1/2010 | ............. C07K 16/12 |
| CN | 101619318 A | | 1/2010 | |
| CN | 102146371 A | | 8/2011 | |
| WO | WO 00/66746 | | 9/2000 | |
| WO | WO 03/013226 A2 | | 2/2003 | |

* cited by examiner

*Primary Examiner* — Russell Kallis
*Assistant Examiner* — Fan Weihua
(74) *Attorney, Agent, or Firm* — Womble Carlyle Sandridge & Rice LLP

(57) ABSTRACT

Disclosed are a method for obtaining highly glyphosate-resistant G1174 gene mutants through artificial mutation and use thereof. Two or more amino acid mutations are introduced in the amino acid sequence from position 95 to position 114 of protein encoded by G1174 gene, and the highly glyphosate-resistant mutants are selected. Also disclosed is a highly glyphosate-resistant mutated G1174 gene, wherein the amino acid sequence from position 95 to position 114 is selected from any one of SEQ ID NO: 4 to SEQ ID NO: 24. The use of the highly glyphosate-resistant mutated gene is for conferring a plant with glyphosate resistance through expression of the transgene in the plant.

8 Claims, No Drawings

HIGHLY GLYPHOSATE-RESISTANT MUTATED GENE, METHOD OF MODIFICATION AND USE THEREOF

CROSS-REFERENCE TO RELATED APPLICATIONS

This application is the U.S. National Stage of International Application PCT/CN2012/070440 filed Jan. 17, 2012, which designates the U.S and was published by the International Bureau in Chinese on Jul. 26, 2012, and which claims the benefit of Chinese Application No. 201110009329.0, filed Jan. 17, 2011, both of which are hereby incorporated by reference in their entirety.

TECHNICAL FIELD

The instant invention falls into the field of plant genetic engineering, and particularly, the instant invention relates to a method for modifying glyphosate-resistant gene, glyphosate-resistant genes and encoded proteins thereof, and a method for obtaining transgenic glyphosate-resistant plant using these modified glyphosate-resistant genes. The invention can be applied to breeding crops and screening plant cell cultures.

BACKGROUND OF THE INVENTION

Glyphosate is a very important herbicide, which inhibits an important enzyme, i.e. 5-enolpyruvylshikimate-3-phosphate synthase (EPSPS), for the biosynthesis of aromatic amino acids in plants. Glyphosate is a herbicide with extremely wide spectrum, which is also lethal to crops. Hence, to perform selective weeding during the growth of crops, the crops have to obtain glyphosate resistance.

Glyphosate can inhibit 5-enolpyruvylshikimate-3-phosphate synthase (EPSPS) of the biosynthesis of aromatic amino acids in majority of bacteria. However, it has been discovered that, EPSPS of partial bacteria has resistance to glyphosate, and the EPSPS of these bacteria has been obtained by separation. Plants can obtain glyphosate resistance by transgenic expression of resistant EPSPS. The resistance obtained by expression of EPSPS of *Agrobacterium* (*Agrobacterium tumefaciens* sp CP4) and *Salmonella typhimurium* CT7 in plants has already been applied in production (U.S. Pat. Nos. 453,590, 4,769,061 and 5,094,945). However, to raise the resistance level of transgenic crops and increase the diversity of resistant gene, new glyphosate-resistant genes and transgenic glyphosate-resistant plants based thereon are still in demand in application in production.

The EPSPS obtained from *Deinococcus radiodurans* R1 has high glyphosate resistance (Chinese Patent 200910098129.x). The invention "A glyphosate-resistant gene and application thereof" filed in 2009 under the application No. 200910098129.x provides a glyphosate-resistant gene, wherein the amino acid sequence of the protein encoded by G1174 gene is as shown in SEQ ID NO: 2 in the patent. Although the glyphosate-resistance of EPSPS of *D. radiodurans* R1 is relative high, it is still very necessary to obtain modified genes of EPSPS with higher resistance. The resistance level conferred to transgenic plants can raise the application dosage of glyphosate, thereby retarding the development of resistant weeds and avoiding hazard caused by dosage problem during the application process.

CONTENTS OF THE INVENTION

The instant patent aims to solve the technical problem of providing a method for modifying glyphosate-resistant EPSPS gene and providing a glyphosate-resistant gene. The resistant gene has higher glyphosate resistance than natural EPSPS gene of *D. radiodurans* R1. The gene can be used for the production of transgenic glyphosate-resistant plants, and can also be used as screening marker in plant cell cultures.

In order to solve the above technical problems, the instant invention is achieved by the following technical solution: the instant invention provides a method for obtaining highly glyphosate-resistant mutated G1174 gene (highly glyphosate-resistant mutated gene) through mutagenesis, wherein two or more amino acid mutations are introduced in the amino acid sequence from position 95 to position 114 (Pro Gly Asn Ala Gly Ala Val Ala Arg Phe Leu Met Gly Val Ala Ala Leu Thr Ser Gly), (SEQ ID NO:31), and the highly glyphosate-resistant mutants are selected. Particularly, two or more mutations at the following positions are introduced: 1) glycine at position 99; 2) alanine at position 100; 3) phenylalanine at position 104; 4) methionine at position 106; and 5) glycine at position 107.

The instant invention also provides a glyphosate-resistant mutated G1174 gene (highly glyphosate-resistant mutated gene), wherein the encoded protein thereof contains at least two mutations at the following positions: 1) mutation of amino acid at position 99 from glycine to alanine; 2) mutation of amino acid at position 100 from alanine to phenylalanine, or threonine, or methionine, or serine; 3) mutation of amino acid at position 104 from phenylalanine to leucine or serine; 4) mutation of amino acid at position 106 from methionine to leucine or serine; and 5) mutation of amino acid at position 107 from glycine to alanine.

The instant invention further provides a glyphosate-resistant mutated G1174 gene (highly glyphosate-resistant mutated gene), wherein the amino acid sequence from position 95 to position 114 of the encoded protein thereof is mutated to at least one of the following sequences: 1) SEQ ID NO: 4, 2) SEQ ID NO: 5, 3) SEQ ID NO: 6, 4) SEQ ID NO: 7, 5) SEQ ID NO: 8, 6) SEQ ID NO: 9, 7) SEQ ID NO: 10, 8) SEQ ID NO: 11, 9) SEQ ID NO: 12, 10) SEQ ID NO: 13, 11) SEQ ID NO: 14, 12) SEQ ID NO: 15, 13) SEQ ID NO: 16, 14) SEQ ID NO: 17, 15) SEQ ID NO: 18, 16) SEQ ID NO: 19, 17) SEQ ID NO: 20, 18) SEQ ID NO: 21, 19) SEQ ID NO: 22, 20) SEQ ID NO: 23, and 21) SEQ ID NO: 24.

The instant invention also provides a highly glyphosate-resistant mutated gene, which has the nucleotide sequence of any one of SEQ ID NO: 26 to SEQ ID NO: 30.

The instant invention also provides a vector containing the above highly glyphosate-resistant mutated gene.

The instant invention further provides a use of the above highly glyphosate-resistant mutated gene: conferring a plant with glyphosate resistance through expression of the transgene in the plant. The plant is rice, maize, cotton, wheat, barley, sorghum, rape, soybean, turf grass or forage grass.

The EPSPS genes originated from *Deinococcus deserti* VCD115 and *Deinococcus geothermalis* (Gene bank: YP_002785524 and YP_604470, polypeptides SEQ ID NO: 4 and SEQ ID NO: 5 provided by the patent application 200910098129.x) have relatively high homology to the G1174 used in the instant invention, and compared with G1174, the amino acid sequences of the encoded proteins thereof are identical to that of G1174 at corresponding positions from position 95 to position 114. The instant invention also provides a method for modifying these homologous genes and other glyphosate-resistant polypeptides with at least 85% similarity to the amino acid sequence of G1174. To obtain proteins with higher glyphosate resistance by screening, at least two of the following mutations can be introduced to these polypeptides at the following positions corresponding to G1174: 1) mutation of amino acid at position 99 from glycine to alanine; 2) mutation of amino acid at position 100 from alanine to phenylalanine, or threonine, or methionine, or serine; 3) mutation of amino acid at position 104 from phenylalanine to leucine or serine; 4) mutation of amino acid at position 106 from methionine to leucine or serine; and 5) mutation of amino acid at position 107 from glycine to alanine.

The instant invention further provides representative nucleotide sequences encoding the highly resistant EPSPS protein mutants: SEQ ID NO: 26, or SEQ ID NO: 27, or SEQ ID NO: 28, or SEQ ID NO: 29, or SEQ ID NO: 30. These genes have DNA fragment encoding chloroplast signal peptide on their 5'-end.

The amino acid sequence of the glyphosate-resistant gene provided by the instant invention can be used in the design and synthesis of nucleotide sequence beneficial to the expression in plants (Campbell and Gowri, Plant Physiol. 92: 1-11), and further constructed to artificial gene expression cassette capable of expressing in plants. The artificial gene expression cassette capable of expressing in plants includes a promoter, a glyphosate-resistant gene with chloroplast signal peptide, and a terminator. The promoter, chloroplast signal peptide and terminator required for the expression and production of glyphosate resistance in plants are known to the prior art. For example, by the transformation of monocotyledon, the promoter can be Ubiqutin-1 promoter of maize or Actin promoter of rice; the terminator can be the terminator from Agrobacterium tumefaciens (Nos) or other terminators; and the signal peptide guiding the glyphosate-resistant protein into the chloroplast can be the signal peptide of subunit of Rubisco (de Castro Silva Filho, 1996, Plant Mol Biol. 30: 767-780), signal peptide of plant EPSPS gene (Archer, 1990, J. Bioenerg. Biomemb. 22 (b): 789-810), and etc. The DNA fragment encoding the chloroplast signal peptide is linked to the 5'-end of a glyphosate-resistant gene and is in an expression cassette. The expression construction can be integrated to a plant genome via Agrobacterium (Agrobacterium strain LAB4404), gene gun method or other methods, and expressed to obtain a glyphosate-resistant plant. The technologies and methods for plant transformation are known and established. The transformation method and procedure are different for different plants. However, generally Agrobacterium and gene gun are used for the introduction into immature embryo, mature embryo, undifferentiated callus or protoplast of a plant. Then a medium containing 1-5 mM glyphosate is used for screening culture. Then transformed seedlings are obtained via differentiation, and transgenic seedlings that can be planted are obtained via culturing in a rooting medium. Furthermore, glyphosate-resistant transgenic plant can be screened by spraying glyphosate.

The instant invention further provides a plasmid containing the above glyphosate-resistant nucleotide sequence molecule, and functionally linked to the nucleotide sequence controlling the expression in a plant to form an expression cassette.

The instant invention further provides a method for modifying plants, including: introducing the above glyphosate-resistant gene expression cassette to plant cells using plant gene transformation technique, and subjecting the cells to a differentiation culture to obtain corresponding transgenic plants. The obtained plants have glyphosate resistance. These plants can be rice, maize, wheat, soybean, rape, sorghum, barley, turf grass or forage grass. The transformation technique for these plants are known in prior art.

The instant invention also provides the use of the nucleotide sequence molecule of the glyphosate-resistant gene for use as screening marker in plant transgenic cell culture.

Another aspect of the instant invention is to provide glyphosate-resistant gene for use as screening marker for gene transfer in plants. The above glyphosate-resistant artificial gene capable of expressing in plant cells can be constructed together with a target gene expression cassette in the same DNA transformation fragment of the same plant transformation plasmid. The target gene can be any valuable gene. The plant expression plasmid can be introduced to a plant tissues with gene gun, Agrobacterium-mediated method or other methods, while a culture medium containing appropriate concentration of glyphosate (for e.g. 1-5 mM) can be used for selective killing of plant cells without the introduced DNA transformation fragment, so as to select plant cells containing the target gene.

The nucleotide sequence of the glyphosate-resistant gene of the instant invention can have many different mutations including but not limited to: 1) different nucleotide sequences obtained by using different codons of the same amino acid, wherein these nucleotide sequences encode protein polypeptides with the same activity; 2) nucleotide sequences obtained by introducing other mutations, wherein these nucleotide sequences still encode proteins with glyphosate resistance. These mutations can be random mutations, or targeted site mutations, or insertion or deletion mutations. One of ordinary skill in the art can generate the above mutations via molecular biological methods.

The instant invention can be applied to all plants including dicotyledon and monocotyledon.

DETAILED DESCRIPTION OF THE PREFERRED EMBODIMENTS

The following specific embodiments are provided for further description of the present invention, but the protection scope of the present invention is not limited thereto.

The molecular biological and biochemical methods applied in the following embodiments are known in the prior art. Detailed descriptions can be found in references such as Ausubel, "Current Protocols in Molecular Biology", John Wiley and Sons Company; J. Sambrookequi et al., "Molecular Cloning: A Labortory Manual" 3rd ED, Cold Spring Harbor Laboratory Press (2001); and etc.

EXAMPLE 1

Expression of EPSPS Gene

The EPSPS gene of Deinococcus, radiodurans (nucleotide sequence SEQ ID NO: 1) was obtained from Sangon Biotech (Shanghai) Co., Ltd through artificial synthesis, and the encoded amino acid sequence is SEQ ID NO: 2. The gene was named G1174, and xmaI and KpnI restriction sites were designed on both ends of the nucleotide fragment of its nucleotide sequence encoding the amino acid from position 95 to position 114.

Vector PMD19 (purchased from TAKARA Company) was used for the expression of G1174 to determine its glyphosate resistance. The G1174 was cloned into PMD19 with general biological method and plasmid vector PMD19-M-1174 was obtained, wherein SEQ ID NO: 3 was the whole sequence of the plasmid vector and sequence of the inserted G1174 gene is 2218-3531. The Escherichia coli TG-1 cells transformed with PMD19 and PMD19-M-1174 were shake-cultured in a LB medium (yeast extract 5.0 g, peptone 10.0 g, sodium chloride 10.0 g, agar 15.0 g, and water to 1.0 L, pH 7.0) at 37° C. for 16 h respectively, then the *Escherichia coli* cells were collected by centrifugation. SDS-PAGE separation was conducted and Western blot was conducted with anti-G1174 antibody. The results showed that no signal was detected by PMD-19, while an obvious signal was detected by PMD19-M-1174, which indicated that the vector can express G1174 protein.

EXAMPLE 2

Obtainment of Mutant Library of EPSPS

To screen EPSPS mutants with higher resistance level, the nucleotide fragment of the amino acid sequence from position 95 to position 114 encoded by G1174 was mutated. The following two degenerate primers were synthesized:

```
                                          (SEQ ID NO: 32)
94-114F: GGG AAC GCG NNG NNG GTG GCC CGC NNC CTG

NNG GNC GTG GCG GCG CTG ACG AGC GGT AC (N represents A\T\G\C).

(SEQ ID NO: 33)
94-114R: C GCT CGT CAG CGC CGC CAC GNC CNN CAG

GNN GCG GGC CAC CNN CGC GTT CCC (N represents

A\T\G\C).
```

The Tris-HCl solutions of the above two nucleotide degenerate primers were mixed, subjected to 5'-end phosphorylation with T4 polynucleotide kinase, then incubated at 65° C. for 20 min, and then cooled to 22° C. to obtain a double-chained DNA fragment capable of linking with a vector restrictively digested with SmaI and KpnI. The DNA fragment was further mixed with SmaI- and KpnI-digested PMD19-M-1174, linked thereto with DNA ligase, and introduced into *Escherichia coli* TG-1 to obtain a mutant library containing different G1174 mutants.

EXAMPLE 3

Screening of Glyphosate Resistance of EPSPS Mutants

A M63 medium containing 60 mM or 100 mM glyphosate was prepared. The formula of the M63 medium was as followed (per L): KH$_2$PO$_4$ 13.6 g, (NH4)$_2$SO$_4$ 2 g, FeSO$_4$-7H$_2$O 0.5 mg, MgCl$_2$ 2.4 mg, glucose 10 g, thiamine-HCl 10 mg and L-proline 25 mg, agar 40 g and distilled water in balance, pH 7.0. After that the M63 medium was sterilized under high temperature and high pressure, and as the temperature was decreased to 55° C., glyphosate was added to a final concentration of 60 mM or 100 mM.

The mutant library containing different G1174 mutants was applied to the M63 medium containing 60 mM glyphosate and cultured. Growth condition was observed 72 h later. The growth of the original G1174 gene on the M63 medium containing 60 mM glyphosate was very slow, and no obvious colony could be observed 72 h later. However partial G1174 mutants were able to grow to visible colonies after cultured for 72 h.

The glyphosate-resistant mutant clones were further cultured in the M63 culture medium containing 100 mM glyphosate. The following clones were able to grow to colonies at 72 h, and they are: G1174-A, G1174-B, G1174-C, G1174-D, G1174-E, G1174-F; G1174-G, G1174-H, G1174-I, G1174-J, G1174-K, G1174-L, G1174-M, G1174-N, G1174-O, G1174-P, G1174-Q, G1174-R, G1174-S, G1174-T, G1174-U, G1174-V and G1174-W.

EXAMPLE 4

Analysis of Mutation Site of Highly Glyphosate-Resistant G1174

The clones that were able to grow normally on 100 mM glyphosate could contain mutants with higher glyphosate resistance than the original G1174 gene. Therefore, nucleotide sequence of the mutation region of the glyphosate-resistant clones obtained from example 3 was determined. The results showed that, the mutation results of these genes were as followed (amino acid from position 95 to position 114):

```
                                          (SEQ ID NO: 34)
G1174:   PGNAGAVARFLMGVAALTSGT (SEQ ID NO: 4)
G1174-A: PGNAGAVARLLMAVAALTSGT (SEQ ID NO: 5)
G1174-B: PGNAGMVARSLLGVAALTSGT (SEQ ID NO: 6)
G1174-C: PGNAAAVARLLMAVAALTSGT (SEQ ID NO: 7)
G1174-D: PGNAAMVARSLMAVAALTSGT (SEQ ID NO: 8)
G1174-E: PGNAGLVARSLLGVAALTSGT (SEQ ID NO: 9)
G1174-F: PGNAAFVARSLMGVAALTSGT (SEQ ID NO: 10)
G1174-G: PGNAASVARFLMGVAALTSGT (SEQ ID NO: 11)
G1174-I: PGNAATVARLLMGVAALTSGT (SEQ ID NO: 12)
G1174-J: PGNAAMVARSLMGVAALTSGT (SEQ ID NO: 13)
G1174-K: PGNAGFVARSLMGVAALTSGT (SEQ ID NO: 14)
G1174-L: PGNAATVARFLMGVAALTSGT (SEQ ID NO: 15)
G1174-M: PGNAAMVARLLMGVAALTSGT (SEQ ID NO: 16)
G1174-N: PGNAGAVARLLLGVAALTSGT (SEQ ID NO: 17)
G1174-O: PGNAGTVARFLLAVAALTSGT (SEQ ID NO: 18)
G1174-P: PGNAGAVARLLLAVAALTSGT (SEQ ID NO: 19)
G1174-R: PGNAGTVARFLTGVAALTSGT (SEQ ID NO: 20)
G1174-S: PGNAGTVARLLSGVAALTSGT (SEQ ID NO: 21)
G1174-T: PGNAGTVARLLLGVAALTSGT
```

```
G1174-U: PGNAAMVARSLLAVAALTSGT    (SEQ ID NO: 22)

G1174-V: PGNAAAVARLLMGVAALTSGT    (SEQ ID NO: 23)

G1174-W: PGNAAFVARSLMAVAALTSGT    (SEQ ID NO: 24)
```

The mutations of these highly glyphosate-resistant mutants included: 1) mutation of amino acid at position 99 from glycine to alanine; 2) mutation of amino acid at position 100 from alanine to phenylalanine, or threonine, or methionine, or serine; 3) mutation of amino acid at position 104 from phenylalanine to leucine or serine; 4) mutation of amino acid at position 106 from methionine to leucine or serine; and 5) mutation of amino acid at position 107 from glycine to alanine. Particularly, these mutations generally contained two or more amino acid mutations.

The previous investigations have discovered that mutation of the amino acid of EPSPS of *Escherichia coli* at position 96 (corresponding to the amino acid of G1174 of the invention at position 99) from glycine to alanine can increase glyphosate resistance, however the activity of the mutated enzyme was reduced (GenBank accession no. X00557; Kishore. et al. 1986; Padgette et al. 1991). To investigate whether high glyphosate resistance can be obtained barely through mutating the amino acid of G1174 gene at position 99 from glycine to alanine, the method of point mutation was applied in the instant invention to obtain a G1174 mutant gene G1174G99A, the amino acid of which is mutated from glycine to alanine at position 99.

To compare the glyphosate resistance of G1174-G99A with G1174-A, G1174-F, G1174-V, and etc. of the instant invention, PMD19 vectors expressing the above mutants were introduced to *Escherichia coli* TG-1, and cultured in an LB medium at 37° C. for 16 h to obtain single colony. Five clones of each mutant were transferred to the M63 medium containing 100 mM glyphosate and cultured at 37° C. for 48 h, and the growth was observed. The results showed that, the growth of the clone expressing G1174-G99A was perspicuously slower than that of the clones expressing G1174-A, G1174-F and G1174-V. At the same time, these expression clones were transferred to the M63 medium containing 100 mM glyphosate (without agarose, other components were the same as the M63 medium), and shake-cultured at 37° C. for 48 h. OD600 was measured, and the results showed that, the OD600 value of G1174-G99A was 0.24, of G1174-A was 0.73, of G1174-F was 0.65 and of G1174-V was 0.53. Hence, the glyphosate-resistant mutants provided by the instant invention showed higher resistance than the sole mutation from glycine to alanine at position 99.

EXAMPLE 5

Construction of Expression Cassette of G1174-A, G1174-C, G1174-L, G1174-O and G1174-V for the Expression in a Plant A codon optimized artificial gene of G1174 suitable for expression in monocotyledon (SEQ ID NO: 25, comprising nucleotide sequence encoding chloroplast signal peptide on the 5'-end) was artificially synthesized. The DNA fragment of the artificial gene has a BamHI site on the 5'-end and a xhoI site on the 3'-end. Corresponding mutations were introduced respectively with prior art mutagenesis method, and G1174 mutant genes containing mutation sites of G1174-A, G1174-C, G1174-L, G1174-O and G1174-V were obtained. (The nucleotide sequences were SEQ ID NO: 26, SEQ ID NO: 27, SEQ ID NO: 28, SEQ ID NO: 29 and SEQ ID NO: 30 respectively.)

The promoter for initiating the expression of G1174 mutant genes was ubiquitin-1 promoter of maize. The promoter was obtained from maize genome by PCR. The primers for PCR were zmUbiF (GCG AAGCTTGCATGCCTACAGTGCAGCGTGACCCGGT-CGTGC, a HindIII site was added, which is represented by the underlined letters) (SEQ ID NO: 35), and zmUbiR (GTG GGATCCTCTAGAGTCGACCTGCA GAAGTAACAC-CAAACAACAG, a BamHI site was added, which is represented by the underlined letters) (SEQ ID NO: 36).

The G1174 mutant genes were restrictively digested with xhoI and BamHI, the ubiquitin-1 promoter of maize obtained by PCR was restrictively digested with HindIII and BamHI, and the both were simultaneously linked to the pCamlbial300 vector restrictively digested with HindIII and xhoI to obtain T-DNA vectors: pCAM1300-1174A, pCAM1300-1174C, pCAM1300-1174L, pCAM1300-1174O and pCAM1300-1174V. The terminator the G1174 mutant genes in the vectors were from the terminator of 35S gene of CaMV from the vectors themselves.

EXAMPLE 6

Transformation of Rice

The prior art (L U, Xiongbin and GONG, Zuxun, 1998, Life Science 10: 125-131; LIU, Fan, et al., 2003, Molecular Plant Breeding 1: 108-115) is adopted in the method for obtaining the transgenic plants. The hulls of mature and full seeds of "Xiu-shui 110" were removed, and calli for use as transformation materials were generated through induction. Agrobacteria containing the vectors pCAM1300-1174A, pCAM1300-1174C, pCAM1300-1174L, pCAM1300-1174O and pCAM1300-1174V were streaked on plates respectively, and single colonies were isolated and inoculated to prepare Agrobacteria for use in transformation. The to-be-transformed calli were placed into an Agrobacteria solution (containing acetosyringone) with appropriate concentration to allow the attachment of Agrobacteria on the surface of the calli, then the calli were transferred to a co-culture medium and co-cultured for 2-3 days. The transformed calli were washed with bacteria-free water, transferred to a selection medium containing appropriate amount of antibiotics, and subjected to a selection culture (2 mM glyphosate) for two months (subculture for once in the middle of the time). The calli with good growth activity after screening were transferred to a pre-differentiation medium and cultured for about 20 days, then the pre-differentiated calli were transferred to a differentiation medium and illuminated for 14 h for differentiation and germination. Two to three weeks later, the resistant regenerated plants were transferred to a rooting medium for hardening seedlings and rooting, and finally the regenerated plants were washed to remove agar and planted in a greenhouse for use as identification materials.

EXAMPLE 7

Transformation of Maize

The transformation method of maize is well established, for e.g. Frame et al. described the transformation method of maize using *Agrobacterium* (Plant Physiol, 2002, 129: 13-22). Agrobacteria containing the vectors pCAM1300-1174A, pCAM1300-1174C, pCAM1300-1174L, pCAM1300-11740 and pCAM1300-1174V were streaked on plates respectively, and single colonies were isolated and inoculated to prepare Agrobacteria for use in transformation. Hi-II corn cobs were collected 8-10 days after pollination. All immature embryos (1.0-1.5 mm in size) were collected. Agrobacteria containing T-DNA vector were bread and cultured together with the immature embryos for 2-3 days (22° C.). The immature embryos were transferred to a callus induction medium (200 mg/L Timentin for killing Agrobacteria) and cultured at 28° C. in the dark for 10-14 days. All calli were transferred to a selection culture medium containing 2 mM glyphosate and cultured at 28° C. in the dark for 2-3 weeks.

All tissues were transferred to a fresh culture medium containing glyphosate and cultured at 28° C. in the dark for 2-3 weeks. Then all embryonic tissues survived from the selection were transferred to a regeneration medium and cultured at 28° C. in the dark for 2-3 weeks with each dish containing one strain. The embryonic tissues were transferred to a fresh regeneration medium and cultured at 26° C. in the light for 10-14 days. All full-developed plants were transferred to a rooting medium, cultured at 26° C. in the light until full development of the roots, then transferred to a greenhouse for single plant cultivation, and the herbicide resistance of the transgenic maize was detected.

EXAMPLE 8

Determination of the Glyphosate Resistance of Transgenic Rice

Ten different transgenic rice strains were selected from transgenic rice obtained from pCAM1300-1174A, pCAM1300-1174C, pCAM1300-1174L, pCAM1300-11740 and pCAM1300-1174V respectively, and planted and cultured in a greenhouse (15-25° C.) together with a non-transgenic strain of "Xiu-shui 110" of the same variety. As the seedlings grew to 10 cm, glyphosate (0.4% w/v) was sprayed at 40 mL/m². Tests were conducted 8 days later, and the results were as in Table 1. The results showed that, the glyphosate resistance of these mutated genes were good.

TABLE 1

Survival rate of transgenic rice after spraying glyphosate.

| Transformed vector | Mortality | % Of growth suppression |
|---|---|---|
| pCAM1300-1174A | 0% | 20% |
| pCAM1300-1174C | 0% | 40% |

TABLE 1-continued

Survival rate of transgenic rice after spraying glyphosate.

| Transformed vector | Mortality | % Of growth suppression |
|---|---|---|
| pCAM1300-1174L | 0% | 60% |
| pCAM1300-1174O | 0% | 40% |
| pCAM1300-1174V | 0% | 20% |
| Parental control | 100% | — |

EXAMPLE 9

Determination of Glyphosate Resistance of Transgenic Maize

Ten different transgenic rice strains were selected respectively from transgenic maize obtained from pCAM1300-1174A, pCAM1300-1174C, pCAM1300-1174L, pCAM1300-11740 and pCAM1300-1174V, and planted and cultivated in a greenhouse (15-25° C.) together with a non-transgenic strain of "Xiu-shui 110" of the same variety. During the seedling stage around 5-6 leaves, glyphosate (0.4% w/v) was sprayed at 40 mL/m². Tests were conducted 8 days later, and the results were as in Table 2. The results showed that, the glyphosate resistance of partial transformed strains of the transgenic maize obtained by using these mutated genes had already reached the level for application in production.

TABLE 2

Survival rate of transgenic maize after spraying glyphosate

| Transformed vector | Mortality | % Of growth suppression |
|---|---|---|
| pCAM1300-1174A | 0% | 40% |
| pCAM1300-1174C | 0% | 40% |
| pCAM1300-1174L | 0% | 70% |
| pCAM1300-1174O | 0% | 50% |
| pCAM1300-1174V | 0% | 60% |
| Parental control | 100% | — |

Finally, it should be noted that, what listed above are only several particular embodiments of the invention. Obviously, the invention is not limited to the above embodiments, and numerous variants are possible thereto. Any variations that can be directly derived or conceived from the content disclosed by the invention by one of ordinary skill in the art, are intended to fall within the scope of the present invention.

The invention claimed is:

1. A method for obtaining a glyphosate-resistant plant, the method comprising:
   a) introducing mutations into a gene encoding a polypeptide having at least 90% sequence identity to SEQ ID NO:2, wherein the mutations result in at least two amino acid modifications between position 95 and position 114 of SEQ ID NO:2 and confer glyphosate-resistance, wherein the at least two amino acid modifications are made at positions selected from the group consisting of; 1) glycine at position 99; 2) alanine at position-100; 3) phenylalanine at position 104; 4)methionine at position 106; and 5)glycine at position 107; and
   b) selecting a glyphosate-resistant plant comprising the at least two amino acid modifications.

2. The method of claim 1, wherein the encoded polypeptide has at least 95% sequence identity to SEQ ID NO:2.

3. The method of claim 1 wherein the at least two amino acid modifications are selected from the group consisting of:
   a) modification of the amino acid at position 99 from glycine to alanine;
   b) modification of the amino acid at position 100 from alanine to phenylalanine or threonine or methionine or serine;
   c) modification of the amino acid at position 104 from phenylalanine to leucine or serine;
   d) modification of the amino acid at position 106 from methionine to leucine or serine; and
   e) modification of the amino acid at position 107 from glycine to alanine.

4. An isolated polypeptide comprising an amino acid sequence having at least 90% sequence identity to SEQ ID NO:2, wherein the amino acid sequence between position 95 and position 114 is selected from the group consisting of SEQ ID NOs:4-24, and wherein the isolated polypeptide confers glyphosate resistance when expressed in a plant.

5. An isolated polynucleotide comprising a nucleotide sequence selected from the group consisting of SEQ ID NOs:26-30.

6. A recombinant DNA vector comprising the polynucleotide of claim 5.

7. A method for obtaining a glyphosate-resistant plant, the method comprising:
   a) transforming a plant with the recombinant DNA vector of claim 6; and
   b) selecting a glyphosate-resistant plant expressing the polynucleotide.

8. The method of claim 7, wherein the plant is rice, maize, cotton, wheat, barley, sorghum, rape, soybean, turf grass or forage grass.

* * * * *

SEQUENCE LISTING

<160> NUMBER OF SEQ ID NOS: 36

<210> SEQ ID NO 1
<211> LENGTH: 1332
<212> TYPE: DNA
<213> ORGANISM: Artificial Sequence
<220> FEATURE:
<223> OTHER INFORMATION: Synthesized

<400> SEQUENCE: 1
atgtccgacg ccctccctgc tacattcgac gtgatcgtgc atccagctcg cgaactccgc      60
ggcgagcttc gcgctcagcc atccaagaac tacaccactc gctacctcct cgccgctgcc     120

-continued

| | |
|---|---|
| ctcgctgagg gcgagacccg cgtggtgggc gtggctacct ctgaggacgc cgaggccatg | 180 |
| ctccgctgcc tccgcgactg gggcgctggc gtggagcttg tgggcgatga cgccgtgatc | 240 |
| cgcggtttcg gcgctcgccc acaggccggt gtgaccctca acccaggcaa cgctggcgca | 300 |
| gtggcccgct tcctcatggg cgtggccgct ctcacctctg gcaccacttt cgtgaccgac | 360 |
| tacccggact ccctcggcaa gcgccctcag ggcgacctcc ttgaggccct cgaacgcctc | 420 |
| ggtgcctggg tgtcctccaa cgacggtcgc ctcccgatct ccgtgtccgg cccagtgcgc | 480 |
| ggtggcaccg tggaggtgtc cgccgagcgc tcctcccagt acgcctccgc cctcatgttc | 540 |
| ctcggccctc tcctcccgga cggactcgaa ctccgcctca ccggcgacat caagtcccac | 600 |
| gctccgctcc gccagacact cgacaccctc tctgacttcg gcgtgcgcgc cactgcctcc | 660 |
| gacgacctcc gccgcatctc catcccgggt ggccagaagt accgcccagg ccgcgtgctc | 720 |
| gtgccgggcg actacccggg ctccgctgcc atcctcaccg ccgctgccct cctcccaggc | 780 |
| gaggtgcgcc tctctaacct ccgcgagcac gacctccagg gcgagaagga ggccgtgaac | 840 |
| gtgctccgcg agatgggcgc tgacatcgtg cgcgaggggc ataccctcac cgtgcgcggt | 900 |
| ggccgccctc tccacgccgt gactcgcgac ggcgattcct tcaccgacgc cgtgcaagcc | 960 |
| ctcaccgccg ctgctgcctt cgccgagggc gacaccacct gggagaacgt ggccactctc | 1020 |
| cgcctcaagg agtgcgaccg catctctgac acccgcgctg agcttgagcg cctcggcctc | 1080 |
| cgcgcacgcg agaccgccga ctctctctcc gtgactggcc tgctcacct cgctggtggc | 1140 |
| atcaccgccg acggccacgg cgaccaccgc atgatcatgc tcctcaccct cctcggcctc | 1200 |
| cgcgcagacg ctccactccg catcaccggc gcacaccaca tccgcaagtc ctaccctcag | 1260 |
| ttcttcgctc acctcgaagc cctcggcgct cgcttcgagt acgctgaggc caccgcctaa | 1320 |
| taggagctcg ag | 1332 |

<210> SEQ ID NO 2
<211> LENGTH: 439
<212> TYPE: PRT
<213> ORGANISM: Artificial Sequence
<220> FEATURE:
<223> OTHER INFORMATION: Synthesized

<400> SEQUENCE: 2

Met Ser Asp Ala Leu Pro Ala Thr Phe Asp Val Ile Val His Pro Ala
 1               5                   10                  15

Arg Glu Leu Arg Gly Glu Leu Arg Ala Gln Pro Ser Lys Asn Tyr Thr
            20                  25                  30

Thr Arg Tyr Leu Leu Ala Ala Ala Leu Ala Glu Gly Glu Thr Arg Val
        35                  40                  45

Val Gly Val Ala Thr Ser Glu Asp Ala Glu Ala Met Leu Arg Cys Leu
    50                  55                  60

Arg Asp Trp Gly Ala Gly Val Glu Leu Val Gly Asp Asp Ala Val Ile
65                  70                  75                  80

Arg Gly Phe Gly Ala Arg Pro Gln Ala Gly Val Thr Leu Asn Pro Gly
                85                  90                  95

Asn Ala Gly Ala Val Ala Arg Phe Leu Met Gly Val Ala Ala Leu Thr
            100                 105                 110

Ser Gly Thr Thr Phe Val Thr Asp Tyr Pro Asp Ser Leu Gly Lys Arg
        115                 120                 125

Pro Gln Gly Asp Leu Leu Glu Ala Leu Glu Arg Leu Gly Ala Trp Val
    130                 135                 140

Ser Ser Asn Asp Gly Arg Leu Pro Ile Ser Val Ser Gly Pro Val Arg
145                 150                 155                 160

Gly Gly Thr Val Glu Val Ser Ala Glu Arg Ser Ser Gln Tyr Ala Ser
                165                 170                 175

Ala Leu Met Phe Leu Gly Pro Leu Leu Pro Asp Gly Leu Glu Leu Arg
            180                 185                 190

Leu Thr Gly Asp Ile Lys Ser His Ala Pro Leu Arg Gln Thr Leu Asp
        195                 200                 205

Thr Leu Ser Asp Phe Gly Val Arg Ala Thr Ala Ser Asp Asp Leu Arg
    210                 215                 220

Arg Ile Ser Ile Pro Gly Gly Gln Lys Tyr Arg Pro Gly Arg Val Leu
225                 230                 235                 240

Val Pro Gly Asp Tyr Pro Gly Ser Ala Ala Ile Leu Thr Ala Ala Ala
                245                 250                 255

Leu Leu Pro Gly Glu Val Arg Leu Ser Asn Leu Arg Glu His Asp Leu
            260                 265                 270

Gln Gly Glu Lys Glu Ala Val Asn Val Leu Arg Glu Met Gly Ala Asp
        275                 280                 285

Ile Val Arg Glu Gly Asp Thr Leu Thr Val Arg Gly Gly Arg Pro Leu
    290                 295                 300

His Ala Val Thr Arg Asp Gly Asp Ser Phe Thr Asp Ala Val Gln Ala
305                 310                 315                 320

Leu Thr Ala Ala Ala Phe Ala Glu Gly Asp Thr Thr Trp Glu Asn
                325                 330                 335

Val Ala Thr Leu Arg Leu Lys Glu Cys Asp Arg Ile Ser Asp Thr Arg
            340                 345                 350

Ala Glu Leu Glu Arg Leu Gly Leu Arg Ala Arg Glu Thr Ala Asp Ser
        355                 360                 365

Leu Ser Val Thr Gly Ser Ala His Leu Ala Gly Ile Thr Ala Asp
    370                 375                 380

Gly His Gly Asp His Arg Met Ile Met Leu Leu Thr Leu Leu Gly Leu
385                 390                 395                 400

Arg Ala Asp Ala Pro Leu Arg Ile Thr Gly Ala His His Ile Arg Lys
                405                 410                 415

Ser Tyr Pro Gln Phe Phe Ala His Leu Glu Ala Leu Gly Ala Arg Phe
            420                 425                 430

Glu Tyr Ala Glu Ala Thr Ala
        435

<210> SEQ ID NO 3
<211> LENGTH: 3684
<212> TYPE: DNA
<213> ORGANISM: Artificial Sequence
<220> FEATURE:
<223> OTHER INFORMATION: Synthesized

<400> SEQUENCE: 3
gacgaaaggg cctcgtgata cgcctatttt tataggttaa tgtcatgata ataatggttt    60
cttagacgtc aggtggcact tttcggggaa atgtgcgcgg aaccccctatt tgtttatttt   120 tctaaataca ttcaaatatg tatccgctca tgagacaata ccctgataa atgcttcaat    180 aatattgaaa aaggaagagt atgagtattc aacatttccg tgtcgccctt attccctttt    240
ttgcggcatt ttgccttcct gttttgctc acccagaaac gctggtgaaa gtaaaagatg    300
ctgaagatca gttgggtgca cgagtgggtt acatcgaact ggatctcaac agcggtaaga    360

```
tccttgagag ttttcgcccc gaagaacgtt ttccaatgat gagcactttt aaagttctgc    420
tatgtggcgc ggtattatcc cgtattgacg ccgggcaaga gcaactcggt cgccgcatac    480
actattctca gaatgacttg gttgagtact caccagtcac agaaaagcat cttacggatg    540
gcatgacagt aagagaatta tgcagtgctg ccataaccat gagtgataac actgcggcca    600
acttacttct gacaacgatc ggaggaccga aggagctaac cgcttttttg cacaacatgg    660
gggatcatgt aactcgcctt gatcgttggg aaccggagct gaatgaagcc ataccaaacg    720
acgagcgtga caccacgatg cctgtagcaa tggcaacaac gttgcgcaaa ctattaactg    780
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc attttaatt taaaaggatc taggtgaaga   1140
tcctttttga taatctcatg accaaaatcc cttaacgtga gttttcgttc cactgagcgt   1200
cagaccccgt agaaaagatc aaaggatctt cttgagatcc ttttttcctg cgcgtaatct   1260
gctgcttgca acaaaaaaa ccaccgctac cagcggtggt ttgtttgccg gatcaagagc   1320
taccaactct ttttccgaag gtaactggct tcagcagagc gcagatacca aatactgttc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg gtcgggctga cggggggtt   1560 cgtgcacaca gcccagcttg gagcgaacga cctacaccga actgagatac ctacagcgtg   1620
agctatgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg attttgtga tgctcgtcag   1800 gggggcggag cctatgggaaa aacgccagca acgcggcctt tttacggttc ctggccttt   1860 gctggccttt tgctcacatg ttctttcctg cgttatcccc tgattctgtg ataaccgta   1920 ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcacccca ggctttacac tttatgcttc   2160
cggctcgtat gttgtgtgga attgtgagcg gataacaatt tcacacagga aacagctatg   2220
gacgccctgc ccgccacctt cgacgtgatc gtgcatccag ctcgcgaact ccgcggcgag   2280
cttcgcgctc agccatccaa gaactacacc actcgctacc tcctcgccgc tgccctcgct   2340
gagggcgaga cccgcgtggt gggcgtggct acctctgagg acgccgaggc catgctccgc   2400
tgcctccgcg actggggcgc tggcgtggag cttgtgggcg atgacgccgt gatccgcggt   2460
ttcggcgctc gccacaggc cggtgtgagg gtcaaccccg ggaacgcggg ggcggtggcc   2520
cgcttcctga tgggcgtggc ggcgctgacg agcggtacca ctttcgtcac cgattacccc   2580
gactcgctcg gcaagcggcc ccaggggat ttgctcgaag ccctggagcg gctggggcg   2640 tgggtgagca gcaacgacgg acgcctccct atctctgtct ccggcccggt gcgcggcggc   2700
accgtcgaag tcagcgccga gcgcagcagc cagtacgcct ccgcgctgat gttcctgggg   2760
```

-continued

```
ccactgctgc cggatggcct ggaactgcgg ctgaccggcg acatcaagag ccacgccccg      2820
ctgcggcaaa cgctcgacac gctgtccgac ttcggcgtgc gggccacggc gagcgacgac      2880
ctgcggcgca tttccattcc cggcgggcaa aagtatcggc ccggacgggt gctggtgccc      2940
ggcgactacc ccggctcggc ggcgattctg acggcggcgg ccctttttgcc cggcgaggtg     3000 cggctctcca acctgcgcga acacgacctg caaggcgaaa aggaggcggt gaacgtgctg      3060
cgcgagatgg cgccgacat cgtgcgggag ggcgacaccc tgacggtgcg cgggggccgc       3120
ccgctgcacg cggtgacgcg cgacggcgac agcttcaccg atgcggtgca ggccctcacc      3180
gccgctgccg ccttcgcgga gggcgacacg acctgggaaa atgtcgccac cctgcgcctc      3240
aaggagtgcg accgcatcag cgacacccgc gccgagctgg agcggctggg cctgcgcgcc      3300
cgcgaaacgg cggacagcct cagcgtgacg ggtagcgccc accttgccgg gggcatcacc      3360
gccgacgggc acggcgacca ccgcatgatc atgctgctga ccctgctggg gctgcgggcc      3420
gacgcgccgc ttcgaattac cggggcgcac cacatccgca agagctatcc gcagttttc     3480 gcccatctgg aagcgctggg ggcgcggttc gagtacgcag aagcgacagc gtaactcgag     3540
taagccagcc ccgacacccg ccaacacccg ctgacgcgcc ctgacgggct tgtctgctcc     3600
cggcatccgc ttacagacaa gctgtgaccg tctccgggag ctgcatgtgt cagaggtttt     3660
caccgtcatc accgaaacgc gcga                                              3684
```

<210> SEQ ID NO 4
<211> LENGTH: 20
<212> TYPE: PRT
<213> ORGANISM: Artificial Sequence
<220> FEATURE:
<223> OTHER INFORMATION: Synthesized

<400> SEQUENCE: 4

Pro Gly Asn Ala Gly Ala Val Ala Arg Leu Leu Met Ala Val Ala Ala
1               5                   10                  15

Leu Thr Ser Gly
            20

<210> SEQ ID NO 5
<211> LENGTH: 20
<212> TYPE: PRT
<213> ORGANISM: Artificial Sequence
<220> FEATURE:
<223> OTHER INFORMATION: Synthesized

<400> SEQUENCE: 5

Pro Gly Asn Ala Gly Met Val Ala Arg Ser Leu Leu Gly Val Ala Ala
1               5                   10                  15

Leu Thr Ser Gly
            20

<210> SEQ ID NO 6
<211> LENGTH: 20
<212> TYPE: PRT
<213> ORGANISM: Artificial Sequence
<220> FEATURE:
<223> OTHER INFORMATION: Synthesized

<400> SEQUENCE: 6

Pro Gly Asn Ala Ala Ala Val Ala Arg Leu Leu Met Ala Val Ala Ala
1               5                   10                  15

Leu Thr Ser Gly

```
                                20

<210> SEQ ID NO 7
<211> LENGTH: 20
<212> TYPE: PRT
<213> ORGANISM: Artificial Sequence
<220> FEATURE:
<223> OTHER INFORMATION: Synthesized

<400> SEQUENCE: 7

Pro Gly Asn Ala Ala Met Val Ala Arg Ser Leu Met Ala Val Ala Ala
 1               5                  10                  15

Leu Thr Ser Gly
          20

<210> SEQ ID NO 8
<211> LENGTH: 20
<212> TYPE: PRT
<213> ORGANISM: Artificial Sequence
<220> FEATURE:
<223> OTHER INFORMATION: Synthesized

<400> SEQUENCE: 8

Pro Gly Asn Ala Gly Leu Val Ala Arg Ser Leu Leu Gly Val Ala Ala
 1               5                  10                  15

Leu Thr Ser Gly
          20

<210> SEQ ID NO 9
<211> LENGTH: 20
<212> TYPE: PRT
<213> ORGANISM: Artificial Sequence
<220> FEATURE:
<223> OTHER INFORMATION: Synthesized

<400> SEQUENCE: 9

Pro Gly Asn Ala Ala Phe Val Ala Arg Ser Leu Met Gly Val Ala Ala
 1               5                  10                  15

Leu Thr Ser Gly
          20

<210> SEQ ID NO 10
<211> LENGTH: 20
<212> TYPE: PRT
<213> ORGANISM: Artificial Sequence
<220> FEATURE:
<223> OTHER INFORMATION: Synthesized

<400> SEQUENCE: 10

Pro Gly Asn Ala Ala Ser Val Ala Arg Phe Leu Met Gly Val Ala Ala
 1               5                  10                  15

Leu Thr Ser Gly
          20

<210> SEQ ID NO 11
<211> LENGTH: 20
<212> TYPE: PRT
<213> ORGANISM: Artificial Sequence
<220> FEATURE:
<223> OTHER INFORMATION: Synthesized

<400> SEQUENCE: 11

Pro Gly Asn Ala Ala Thr Val Ala Arg Leu Leu Met Gly Val Ala Ala
 1               5                  10                  15
```

Leu Thr Ser Gly
        20

<210> SEQ ID NO 12
<211> LENGTH: 20
<212> TYPE: PRT
<213> ORGANISM: Artificial Sequence
<220> FEATURE:
<223> OTHER INFORMATION: Synthesized

<400> SEQUENCE: 12

Pro Gly Asn Ala Ala Met Val Ala Arg Ser Leu Met Gly Val Ala Ala
1               5                   10                  15

Leu Thr Ser Gly
        20

<210> SEQ ID NO 13
<211> LENGTH: 20
<212> TYPE: PRT
<213> ORGANISM: Artificial Sequence
<220> FEATURE:
<223> OTHER INFORMATION: Synthesized

<400> SEQUENCE: 13

Pro Gly Asn Ala Gly Phe Val Ala Arg Ser Leu Met Gly Val Ala Ala
1               5                   10                  15

Leu Thr Ser Gly
        20

<210> SEQ ID NO 14
<211> LENGTH: 20
<212> TYPE: PRT
<213> ORGANISM: Artificial Sequence
<220> FEATURE:
<223> OTHER INFORMATION: Synthesized

<400> SEQUENCE: 14

Pro Gly Asn Ala Ala Thr Val Ala Arg Phe Leu Met Gly Val Ala Ala
1               5                   10                  15

Leu Thr Ser Gly
        20

<210> SEQ ID NO 15
<211> LENGTH: 20
<212> TYPE: PRT
<213> ORGANISM: Artificial Sequence
<220> FEATURE:
<223> OTHER INFORMATION: Synthesized

<400> SEQUENCE: 15

Pro Gly Asn Ala Ala Met Val Ala Arg Leu Leu Met Gly Val Ala Ala
1               5                   10                  15

Leu Thr Ser Gly
        20

<210> SEQ ID NO 16
<211> LENGTH: 20
<212> TYPE: PRT
<213> ORGANISM: Artificial Sequence
<220> FEATURE:
<223> OTHER INFORMATION: Synthesized

<400> SEQUENCE: 16

Pro Gly Asn Ala Gly Ala Val Ala Arg Leu Leu Leu Gly Val Ala Ala
1               5                   10                  15

Leu Thr Ser Gly
        20

<210> SEQ ID NO 17
<211> LENGTH: 20
<212> TYPE: PRT
<213> ORGANISM: Artificial Sequence
<220> FEATURE:
<223> OTHER INFORMATION: Synthesized

<400> SEQUENCE: 17

Pro Gly Asn Ala Gly Thr Val Ala Arg Phe Leu Leu Ala Val Ala Ala
1               5                   10                  15

Leu Thr Ser Gly
        20

<210> SEQ ID NO 18
<211> LENGTH: 20
<212> TYPE: PRT
<213> ORGANISM: Artificial Sequence
<220> FEATURE:
<223> OTHER INFORMATION: Synthesized

<400> SEQUENCE: 18

Pro Gly Asn Ala Gly Ala Val Ala Arg Leu Leu Leu Ala Val Ala Ala
1               5                   10                  15

Leu Thr Ser Gly
        20

<210> SEQ ID NO 19
<211> LENGTH: 20
<212> TYPE: PRT
<213> ORGANISM: Artificial Sequence
<220> FEATURE:
<223> OTHER INFORMATION: Synthesized

<400> SEQUENCE: 19

Pro Gly Asn Ala Gly Thr Val Ala Arg Phe Leu Thr Gly Val Ala Ala
1               5                   10                  15

Leu Thr Ser Gly
        20

<210> SEQ ID NO 20
<211> LENGTH: 20
<212> TYPE: PRT
<213> ORGANISM: Artificial Sequence
<220> FEATURE:
<223> OTHER INFORMATION: Synthesized

<400> SEQUENCE: 20

Pro Gly Asn Ala Gly Thr Val Ala Arg Leu Leu Ser Gly Val Ala Ala
1               5                   10                  15

Leu Thr Ser Gly
        20

<210> SEQ ID NO 21
<211> LENGTH: 20
<212> TYPE: PRT
<213> ORGANISM: Artificial Sequence
<220> FEATURE:
<223> OTHER INFORMATION: Synthesized

<400> SEQUENCE: 21

Pro Gly Asn Ala Gly Thr Val Ala Arg Leu Leu Leu Gly Val Ala Ala

```
                    1               5                   10                  15

Leu Thr Ser Gly
            20

<210> SEQ ID NO 22
<211> LENGTH: 20
<212> TYPE: PRT
<213> ORGANISM: Artificial Sequence
<220> FEATURE:
<223> OTHER INFORMATION: Synthesized

<400> SEQUENCE: 22

Pro Gly Asn Ala Ala Met Val Ala Arg Ser Leu Leu Ala Val Ala Ala
  1               5                   10                  15

Leu Thr Ser Gly
            20

<210> SEQ ID NO 23
<211> LENGTH: 20
<212> TYPE: PRT
<213> ORGANISM: Artificial Sequence
<220> FEATURE:
<223> OTHER INFORMATION: Synthesized

<400> SEQUENCE: 23

Pro Gly Asn Ala Ala Ala Val Ala Arg Leu Leu Met Gly Val Ala Ala
  1               5                   10                  15

Leu Thr Ser Gly
            20

<210> SEQ ID NO 24
<211> LENGTH: 20
<212> TYPE: PRT
<213> ORGANISM: Artificial Sequence
<220> FEATURE:
<223> OTHER INFORMATION: Synthesized

<400> SEQUENCE: 24

Pro Gly Asn Ala Ala Phe Val Ala Arg Ser Leu Met Ala Val Ala Ala
  1               5                   10                  15

Leu Thr Ser Gly
            20

<210> SEQ ID NO 25
<211> LENGTH: 1536
<212> TYPE: DNA
<213> ORGANISM: Artificial Sequence
<220> FEATURE:
<223> OTHER INFORMATION: Synthesized

<400> SEQUENCE: 25
ggatccacca tggccaccgc cgccgccgcg tctaccgcgc tcactggcgc cactaccgct      60
gcgcccaagg cgaggcgccg ggcgcacctc ctggccaccc gccgcgccct cgccgcgccc     120
atcaggtgct cagcggcgtc accgccatgc cgatggctc ccccggccac cccgctccgg      180
ccgtggggcc ccaccgatcc ccgcaagaga tccgacgccc tgcccgccac cttcgacgtg     240
atcgtgcatc cagctcgcga actccgcggc gagcttcgcg ctcagccatc caagaactac     300
accactcgct acctcctcgc cgctgccctc gctgagggcg agaccgcgt ggtgggcgtg      360 gctacctctg aggacgccga ggccatgctc cgctgcctcc gcgactgggg cgctggcgtg     420
gagcttgtgg gcgatgacgc cgtgatccgc ggtttcggcg ctcgcccaca ggccggtgtg     480
```

| | |
|---|---|
| accctcaacc caggcaacgc tggcgcggtg gcccgcttcc tcatgggcgt ggccgctctc | 540 |
| acctctggca ccactttcgt gaccgactac ccggactccc tcggcaagcg ccctcagggc | 600 |
| gacctccttg aggccctcga acgcctcggt gcctgggtgt cctccaacga cggtcgcctc | 660 |
| ccgatctccg tgtccggccc agtgcgcggt ggcaccgtgg aggtgtccgc cgagcgctcc | 720 |
| tcccagtacg cctccgccct catgttcctc ggccctctcc tcccggacgg actcgaactc | 780 |
| cgcctcaccg gcgacatcaa gtcccacgct ccgctccgcc agacactcga caccctctct | 840 |
| gacttcggcg tgcgcgccac tgcctccgac gacctccgcc gcatctccat cccgggtggc | 900 |
| cagaagtacc gcccaggccg cgtgctcgtg ccgggcgact acccgggctc cgctgccatc | 960 |
| ctcaccgccg ctgccctcct cccaggcgag gtgcgcctct ctaacctccg cgagcacgac | 1020 |
| ctccagggcg agaaggaggc cgtgaacgtg ctccgcgaga tgggcgctga catcgtgcgc | 1080 |
| gagggcgata ccctcaccgt gcgcggtggc cgccctctcc acgccgtgac tcgcgacggc | 1140 |
| gattccttca ccgacgccgt gcaagccctc accgccgctg ctgccttcgc cgagggcgac | 1200 |
| accacctggg agaacgtggc cactctccgc ctcaaggagt gcgaccgcat ctctgacacc | 1260 |
| cgcgctgagc ttgagcgcct cggcctccgc gcacgcgaga ccgccgactc tctctccgtg | 1320 |
| actggctctg ctcacctcgc tggtggcatc accgccgacg ccacggcga ccaccgcatg | 1380 |
| atcatgctcc tcaccctcct cggcctccgc gcagacgctc cactccgcat caccggcgca | 1440 |
| caccacatcc gcaagtccta ccctcagttc ttcgctcacc tcgaagccct cggcgctcgc | 1500 |
| ttcgagtacg ctgaggccac cgcctaatag ctcgag | 1536 |

<210> SEQ ID NO 26
<211> LENGTH: 1536
<212> TYPE: DNA
<213> ORGANISM: Artificial Sequence
<220> FEATURE:
<223> OTHER INFORMATION: Synthesized

<400> SEQUENCE: 26

| | |
|---|---|
| ggatccacca tggccaccgc cgccgccgcg tctaccgcgc tcactggcgc cactaccgct | 60 |
| gcgcccaagg cgaggcgccg ggcgcacctc ctggccaccc gccgcgccct cgccgcgccc | 120 |
| atcaggtgct cagcggcgtc accgccatg ccgatggctc cccggccac cccgctccgg | 180 |
| ccgtggggcc ccaccgatcc ccgcaagaga tccgacgccc tgcccgccac cttcgacgtg | 240 |
| atcgtgcatc cagctcgcga actccgcggc gagcttcgcg ctcagccatc caagaactac | 300 |
| accactcgct acctcctcgc cgctgcccte gctgagggcg agaccccgcgt ggtgggcgtg | 360 |
| gctacctctg aggacgccga ggccatgctc cgctgcctcc gcgactgggg cgctggcgtg | 420 |
| gagcttgtgg gcgatgacgc cgtgatccgc ggtttcggcg ctcgcccaca ggccggtgtg | 480 |
| accctcaacc caggcaacgc tggcgcggtg gcccgcctcc tcatggccgt ggccgctctc | 540 |
| acctctggca ccactttcgt gaccgactac ccggactccc tcggcaagcg ccctcagggc | 600 |
| gacctccttg aggccctcga acgcctcggt gcctgggtgt cctccaacga cggtcgcctc | 660 |
| ccgatctccg tgtccggccc agtgcgcggt ggcaccgtgg aggtgtccgc cgagcgctcc | 720 |
| tcccagtacg cctccgccct catgttcctc ggccctctcc tcccggacgg actcgaactc | 780 |
| cgcctcaccg gcgacatcaa gtcccacgct ccgctccgcc agacactcga caccctctct | 840 |
| gacttcggcg tgcgcgccac tgcctccgac gacctccgcc gcatctccat cccgggtggc | 900 |
| cagaagtacc gcccaggccg cgtgctcgtg ccgggcgact acccgggctc cgctgccatc | 960 |
| ctcaccgccg ctgccctcct cccaggcgag gtgcgcctct ctaacctccg cgagcacgac | 1020 |

| | |
|---|---|
| ctccagggcg agaaggaggc cgtgaacgtg ctccgcgaga tgggcgctga catcgtgcgc | 1080 |
| gagggcgata ccctcaccgt gcgcggtggc cgccctctcc acgccgtgac tcgcgacggc | 1140 |
| gattccttca ccgacgccgt gcaagccctc accgccgctg ctgccttcgc cgagggcgac | 1200 |
| accacctggg agaacgtggc cactctccgc ctcaaggagt gcgaccgcat ctctgacacc | 1260 |
| cgcgctgagc ttgagcgcct cggcctccgc gcacgcgaga ccgccgactc tctctccgtg | 1320 |
| actggctctg ctcacctcgc tggtggcatc accgccgacg ccacggcga ccaccgcatg | 1380 |
| atcatgctcc tcaccctcct cggcctccgc gcagacgctc cactccgcat caccggcgca | 1440 |
| caccacatcc gcaagtccta ccctcagttc ttcgctcacc tcgaagccct cggcgctcgc | 1500 |
| ttcgagtacg ctgaggccac cgcctaatag ctcgag | 1536 |

<210> SEQ ID NO 27
<211> LENGTH: 1536
<212> TYPE: DNA
<213> ORGANISM: Artificial Sequence
<220> FEATURE:
<223> OTHER INFORMATION: Synthesized

<400> SEQUENCE: 27

| | |
|---|---|
| ggatccacca tggccaccgc cgccgccgcg tctaccgcgc tcactggcgc cactaccgct | 60 |
| gcgcccaagg cgaggcgccg ggcgcacctc ctggccaccc gccgcgccct cgccgcgccc | 120 |
| atcaggtgct cagcggcgtc accgccatg ccgatggctc cccggccac cccgctccgg | 180 |
| ccgtggggcc ccaccgatcc ccgcaagaga tccgacgccc tgcccgccac cttcgacgtg | 240 |
| atcgtgcatc cagctcgcga actccgcggc gagcttcgcg ctcagccatc caagaactac | 300 |
| accactcgct acctcctcgc cgctgccctc gctgagggcg agaccccgcgt ggtgggcgtg | 360 |
| gctacctctg aggacgccga ggccatgctc cgctgcctcc gcgactgggg cgctggcgtg | 420 |
| gagcttgtgg gcgatgacgc cgtgatccgc ggtttcggcg ctcgcccaca ggccggtgtg | 480 |
| accctcaacc caggcaacgc tgccgcggtg cccgcctcc tcatggccgt ggccgctctc | 540 |
| acctctggca ccactttcgt gaccgactac ccggactccc tcggcaagcg ccctcagggc | 600 |
| gacctccttg aggccctcga acgcctcggt gcctgggtgt cctccaacga cggtcgcctc | 660 |
| ccgatctccg tgtccggccc agtgcgcggt ggcaccgtgg aggtgtccgc cgagcgctcc | 720 |
| tcccagtacg cctccgccct catgttcctc ggccctctcc tcccggacgg actcgaactc | 780 |
| cgcctcaccg gcgacatcaa gtcccacgct ccgctccgcc agacactcga caccctctct | 840 |
| gacttcggcc tgcgcgccac tgcctccgac gacctccgcc gcatctccat cccgggtggc | 900 |
| cagaagtacc gcccaggccg cgtgctcgtg ccgggcgact accgggctc cgctgccatc | 960 |
| ctcaccgccc tgccctcct cccaggcgag gtgcgcctct ctaacctccg cgagcacgac | 1020 |
| ctccagggcg agaaggaggc cgtgaacgtg ctccgcgaga tgggcgctga catcgtgcgc | 1080 |
| gagggcgata ccctcaccgt gcgcggtggc cgccctctcc acgccgtgac tcgcgacggc | 1140 |
| gattccttca ccgacgccgt gcaagccctc accgccgctg ctgccttcgc cgagggcgac | 1200 |
| accacctggg agaacgtggc cactctccgc ctcaaggagt gcgaccgcat ctctgacacc | 1260 |
| cgcgctgagc ttgagcgcct cggcctccgc gcacgcgaga ccgccgactc tctctccgtg | 1320 |
| actggctctg ctcacctcgc tggtggcatc accgccgacg ccacggcga ccaccgcatg | 1380 |
| atcatgctcc tcaccctcct cggcctccgc gcagacgctc cactccgcat caccggcgca | 1440 |
| caccacatcc gcaagtccta ccctcagttc ttcgctcacc tcgaagccct cggcgctcgc | 1500 |

| | |
|---|---:|
| ttcgagtacg ctgaggccac cgcctaatag ctcgag | 1536 |

<210> SEQ ID NO 28
<211> LENGTH: 1536
<212> TYPE: DNA
<213> ORGANISM: Artificial Sequence
<220> FEATURE:
<223> OTHER INFORMATION: Synthesized

<400> SEQUENCE: 28

| | |
|---|---:|
| ggatccacca tggccaccgc cgccgccgcg tctaccgcgc tcactggcgc cactaccgct | 60 |
| gcgcccaagg cgaggcgccg ggcgcacctc ctggccaccc gccgcgccct cgccgcgccc | 120 |
| atcaggtgct cagcggcgtc acccgccatg ccgatggctc ccccggccac cccgctccgg | 180 |
| ccgtggggcc ccaccgatcc ccgcaagaga tccgacgccc tgcccgccac cttcgacgtg | 240 |
| atcgtgcatc cagctcgcga actccgcggc gagcttcgcg ctcagccatc caagaactac | 300 |
| accactcgct acctcctcgc cgctgccctc gctgagggcg agaccgcgt ggtgggcgtg | 360 |
| gctacctctg aggacgccga ggccatgctc cgctgcctcc gcgactgggg cgctggcgtg | 420 |
| gagcttgtgg gcgatgacgc cgtgatccgc ggtttcggcg ctcgcccaca ggccggtgtg | 480 |
| accctcaacc caggcaacgc tgccacggtg gcccgcttcc tcatgggcgt ggccgctctc | 540 |
| acctctggca ccactttcgt gaccgactac ccggactccc tcggcaagcg ccctcagggc | 600 |
| gacctccttg aggccctcga acgctcggtg gcctgggtgt cctccaacga cggtcgcctc | 660 |
| ccgatctccg tgtccggccc agtgcgcggt ggcaccgtgg aggtgtccgc cgagcgctcc | 720 |
| tcccagtacg cctccgccct catgttcctc ggccctctcc tcccggacgg actcgaactc | 780 |
| cgcctcaccg gcgacatcaa gtcccacgct ccgctccgcc agacactcga caccctctct | 840 |
| gacttcggcg tgcgcgccac tgcctccgac gacctccgcc gcatctccat cccgggtggc | 900 |
| cagaagtacc gcccaggccg cgtgctcgtg ccgggcgact acccgggctc cgctgccatc | 960 |
| ctcaccgccg ctgccctcct cccaggcgag gtgcgcctct ctaacctccg cgagcacgac | 1020 |
| ctccagggcg agaaggaggc cgtgaacgtg ctccgcgaga tgggcgctga catcgtgcgc | 1080 |
| gagggcgata ccctcaccgt gcgcggtggc cgccctctcc acgccgtgac tcgcgacggc | 1140 |
| gattccttca ccgacgccgt gcaagccctc accgccgctg ctgccttcgc cgagggcgac | 1200 |
| accacctggg agaacgtggc cactctccgc ctcaaggagt gcgaccgcat ctctgacacc | 1260 |
| cgcgctgagc ttgagcgcct cggcctccgc gcacgcgaga ccgccgactc tctctccgtg | 1320 |
| actggctctg ctcacctcgc tggtggcatc accgccgacg ccacggcga ccaccgcatg | 1380 |
| atcatgctcc tcaccctcct cggcctccgc gcagacgctc cactccgcat caccggcgca | 1440 |
| caccacatcc gcaagtccta ccctcagttc ttcgctcacc tcgaagccct cggcgctcgc | 1500 |
| ttcgagtacg ctgaggccac cgcctaatag ctcgag | 1536 |

<210> SEQ ID NO 29
<211> LENGTH: 1536
<212> TYPE: DNA
<213> ORGANISM: Artificial Sequence
<220> FEATURE:
<223> OTHER INFORMATION: Synthesized

<400> SEQUENCE: 29

| | |
|---|---:|
| ggatccacca tggccaccgc cgccgccgcg tctaccgcgc tcactggcgc cactaccgct | 60 |
| gcgcccaagg cgaggcgccg ggcgcacctc ctggccaccc gccgcgccct cgccgcgccc | 120 |
| atcaggtgct cagcggcgtc acccgccatg ccgatggctc ccccggccac cccgctccgg | 180 | ccgtggggcc ccaccgatcc ccgcaagaga tccgacgccc tgcccgccac cttcgacgtg    240 atcgtgcatc cagctcgcga actccgcggc gagcttcgcg ctcagccatc aagaactac    300 accactcgct acctcctcgc cgctgccctc gctgagggcg agaccccgcgt ggtgggcgtg    360 gctacctctg aggacgccga ggccatgctc cgctgcctcc gcgactgggg cgctggcgtg    420 gagcttgtgg gcgatgacgc cgtgatccgc ggtttcggcg ctcgcccaca ggccggtgtg    480 accctcaacc caggcaacgc tgccacgtg gcccgcctcc tcatgggcgt ggccgctctc    540 acctctggca ccactttcgt gaccgactac ccggactccc tcggcaagcg ccctcagggc    600 gacctccttg aggccctcga acgcctcggt gcctgggtgt cctccaacga cggtcgcctc    660 ccgatctccg tgtccggccc agtgcgcggt ggcaccgtgg aggtgtccgc cgagcgctcc    720 tcccagtacg cctccgccct catgttcctc ggccctctcc tcccggacgg actcgaactc    780 cgcctcaccg gcgacatcaa gtcccacgct ccgctccgcc agacactcga caccctctct    840 gacttcggcg tgcgcgccac tgcctccgac gacctccgcc gcatctccat cccgggtggc    900 cagaagtacc gcccaggccg cgtgctcgtg ccgggcgact acccgggctc cgctgccatc    960 ctcaccgccg ctgccctcct cccaggcgag gtgcgcctct ctaacctccg cgagcacgac   1020 ctccagggcg agaaggaggc cgtgaacgtg ctccgcgaga tgggcgctga catcgtgcgc   1080 gagggcgata ccctcaccgt gcgcggtggc cgccctctcc acgccgtgac tcgcgacggc   1140 gattccttca ccgacgccgt gcaagccctc accgccgctg ctgccttcgc cgagggcgac   1200 accacctggg agaacgtggc cactctccgc ctcaaggagt gcgaccgcat ctctgacacc   1260 cgcgctgagc ttgagcgcct cggcctccgc gcacgcgaga ccgccgactc tctctccgtg   1320 actggctctg ctcacctcgc tggtggcatc accgccgacg gccacggcga ccaccgcatg   1380 atcatgctcc tcaccctcct cggcctccgc gcagacgctc cactccgcat caccggcgca   1440 caccacatcc gcaagtccta ccctcagttc ttcgctcacc tcgaagccct cggcgctcgc   1500 ttcgagtacg ctgaggccac cgcctaatag ctcgag   1536

<210> SEQ ID NO 30
<211> LENGTH: 1536
<212> TYPE: DNA
<213> ORGANISM: Artificial Sequence
<220> FEATURE:
<223> OTHER INFORMATION: Synthesized

<400> SEQUENCE: 30
ggatccacca tggccaccgc cgccgccgcg tctaccgcgc tcactggcgc cactaccgct     60
gcgcccaagg cgaggcgccg ggcgcacctc ctggccaccc gccgcgccct cgccgcgccc    120
atcaggtgct cagcggcgtc accgccatg ccgatggctc ccccgccac cccgctccgg    180 ccgtggggcc ccaccgatcc ccgcaagaga tccgacgccc tgcccgccac cttcgacgtg    240
atcgtgcatc cagctcgcga actccgcggc gagcttcgcg ctcagccatc aagaactac    300 accactcgct acctcctcgc cgctgccctc gctgagggcg agaccccgcgt ggtgggcgtg    360 gctacctctg aggacgccga ggccatgctc cgctgcctcc gcgactgggg cgctggcgtg    420
gagcttgtgg gcgatgacgc cgtgatccgc ggtttcggcg ctcgcccaca ggccggtgtg    480
accctcaacc caggcaacgc tgccgcggtg gcccgcctcc tcatgggcgt ggccgctctc    540
acctctggca ccactttcgt gaccgactac ccggactccc tcggcaagcg ccctcagggc    600
gacctccttg aggccctcga acgcctcggt gcctgggtgt cctccaacga cggtcgcctc    660

```
ccgatctccg tgtccggccc agtgcgcggt ggcaccgtgg aggtgtccgc cgagcgctcc      720
tcccagtacg cctccgccct catgttcctc ggccctctcc tcccggacgg actcgaactc      780
cgcctcaccg gcgacatcaa gtcccacgct ccgctccgcc agacactcga caccctctct      840
gacttcggcg tgcgcgccac tgcctccgac gacctccgcc gcatctccat cccgggtggc      900
cagaagtacc gcccaggccg cgtgctcgtg ccgggcgact acccgggctc cgctgccatc      960
ctcaccgccg ctgccctcct cccaggcgag gtgcgcctct ctaacctccg cgagcacgac     1020
ctccagggcg agaaggaggc cgtgaacgtg ctccgcgaga tgggcgctga catcgtgcgc     1080
gagggcgata ccctcaccgt gcgcggtggc cgccctctcc acgccgtgac tcgcgacggc     1140
gattccttca ccgacgccgt gcaagccctc accgccgctg ctgccttcgc cgagggcgac     1200
accacctggg agaacgtggc cactctccgc ctcaaggagt cgaccgcat  ctctgacacc     1260 cgcgctgagc ttgagcgcct cggcctccgc gcacgcgaga ccgccgactc tctctccgtg     1320
actggctctg ctcacctcgc tggtggcatc accgccgacg gccacggcga ccaccgcatg     1380
atcatgctcc tcaccctcct cggcctccgc gcagacgctc cactccgcat caccggcgca     1440
caccacatcc gcaagtccta ccctcagttc ttcgctcacc tcgaagccct cggcgctcgc     1500
ttcgagtacg ctgaggccac cgcctaatag ctcgag                              1536
```

<210> SEQ ID NO 31
<211> LENGTH: 20
<212> TYPE: PRT
<213> ORGANISM: Artificial Sequence
<220> FEATURE:
<223> OTHER INFORMATION: Synthesized

<400> SEQUENCE: 31

Pro Gly Asn Ala Gly Ala Val Ala Arg Phe Leu Met Gly Val Ala Ala
 1               5                  10                  15

Leu Thr Ser Gly
            20

<210> SEQ ID NO 32
<211> LENGTH: 59
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: 10, 11, 13, 14, 25, 26, 31, 32, 35
<223> OTHER INFORMATION: n = A,T,C or G

<400> SEQUENCE: 32
gggaacgcgn ngnnggtggc ccgcnncctg nnggncgtgg cggcgctgac gagcggtac      59

<210> SEQ ID NO 33
<211> LENGTH: 52
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: 21, 24, 25, 30, 31, 42, 43
<223> OTHER INFORMATION: n = A,T,C or G

<400> SEQUENCE: 33
cgctcgtcag cgccgccacg nccnncaggn ngcgggccac cnncgcgttc cc             52

```
<210> SEQ ID NO 34
<211> LENGTH: 21
<212> TYPE: PRT
<213> ORGANISM: Artificial Sequence
<220> FEATURE:
<223> OTHER INFORMATION: Synthesized

<400> SEQUENCE: 34

Pro Gly Asn Ala Gly Ala Val Ala Arg Phe Leu Met Gly Val Ala Ala
 1               5                  10                  15

Leu Thr Ser Gly Thr
            20

<210> SEQ ID NO 35
<211> LENGTH: 41
<212> TYPE: DNA
<213> ORGANISM: Artificial Sequence
<220> FEATURE:
<223> OTHER INFORMATION: Synthesized

<400> SEQUENCE: 35
cgaagcttgc atgcctacag tgcagcgtga cccggtcgtg c                         41

<210> SEQ ID NO 36
<211> LENGTH: 45
<212> TYPE: DNA
<213> ORGANISM: Artificial Sequence
<220> FEATURE:
<223> OTHER INFORMATION: Synthesized

<400> SEQUENCE: 36
gtgggatcct ctagagtcga cctgcagaag taacaccaaa caaca                    45
```